United States Patent [19]
Thomas, Jr. et al.

[11] Patent Number: 5,607,964
[45] Date of Patent: Mar. 4, 1997

[54] CLINICAL MARKER AND THERAPEUTIC AGENT IN KIDNEY STONE DISEASE AND METHODS OF USE

[75] Inventors: William C. Thomas, Jr.; Christopher D. Batich; Daniel L. Purich, all of Gainesville, Fla.

[73] Assignee: University of Florida, Gainesville, Fla.

[21] Appl. No.: 458,368

[22] Filed: Jun. 2, 1995

Related U.S. Application Data

[62] Division of Ser. No. 261,581, Jun. 17, 1994.
[51] Int. Cl.$^6$ .................................................. A61K 31/335
[52] U.S. Cl. .................................................. 514/452
[58] Field of Search ........................................ 514/452

[56] References Cited

U.S. PATENT DOCUMENTS

| | | | |
|---|---|---|---|
| 4,399,003 | 8/1983 | Sarig et al. | 204/1 T |
| 4,888,182 | 12/1989 | Pak | 424/677 |
| 5,137,722 | 8/1992 | Costello | 424/195.1 |

FOREIGN PATENT DOCUMENTS

| | | |
|---|---|---|
| 0206626 | 12/1986 | European Pat. Off. . |
| 8604815 | 8/1986 | WIPO . |
| 9005713 | 5/1990 | WIPO . |

OTHER PUBLICATIONS

Boyce, W. H. (1979) "Epidemiology of Lithiasis in the United States" XVIIIth C.M. Congress of the International Society of Urology, Paris, Kongressbericht, Tome 1, pp. 79–86.

Sierakowski, R. et al. (1978) "The Frequency of Urolithiasis in Hospital Discharge Diagnoses in the United States" Investigative Urology 15(6):438–441.

Thomas, W. C. Jr. (1976) "Renal Calculi: A Guide to Management", Charles C. Thomas, Publisher, Springfield, IL, 177 pages.

Davis, Geroge K. et al. (1974) "Urolithiasis", Geochemistry and the Environment, National Academy of Science, Washington, pp. 133–138.

Zhmurov, V. A. et al. (1991) "Parameters of Destabilized Cellular Membrane and Urolithiasis" Urol. Nefrol–Moscow May–Jun. (3):12–15.

Azoury, R. et al. (1990) "Hydration Feature of Urinary Compounds" Urological Research 18:7–11.

Schrier, E. E. et al. (1979) "Macromolecular Inhibitors of Calcium Oxalate Crystal Growth and Aggregation in Urine" Oxalate in Human Biochemistry and Clinical Pathology, pp. 22–27.

Bose, P. K., S. N. Bhatacharyya (1936) "On the Constitution of an Acid Isolated from Pineapple" Science and Culture 2:162.

Thomas, William Thomas, Jr. MD (1988) "Kidney Stones, Urine, and Cement" American Journal Kidney Disease 37(11):861–862.

Coe, F. L. et al. (1991) "Inhibitors Within the Nephron" American Journal of Kidney Diseases 17(4):407–413.

Lewis, B. D. (1990) "Determination of Citrate in Urine by Simple Direct Photometry–Letters to the Editor" Clinical Chemistry 35(3):578.

Varaprasad, D. V. P. R. et al. (1986) "Synthesis of polyfunctional hydroxmic acids for potential use in iron chelation therapy" Chemical Abstracts 105(1):43, abstract No. 458.

Millan, A. et al. (1987) "Determination of Citrate in Urine by Simple Direct Photometry" Clinical Chemistry 33(7):1259–1260.

*Primary Examiner*—Phyllis G. Spivack
*Attorney, Agent, or Firm*—Saliwanchik & Saliwanchik

[57] ABSTRACT

Treating patients prophylactically and therapeutically with dicitrate cyclic diester (dicitrate) can prevent or reduce the effects of calcification-related disease, including some types of kidney stones.

8 Claims, 2 Drawing Sheets

5,607,964

CLINICAL MARKER AND THERAPEUTIC AGENT IN KIDNEY STONE DISEASE AND METHODS OF USE

This invention was made with government support under National Institutes of Health Research Grant No. P01-DK20586; and with support from Veteran Affairs Medical Center, Gainesville, Fla. The government has certain rights in this invention.

This is a division, of application Ser. No. 08/261,581, filed Jun. 17, 1994.

CROSS-REFERENCE TO A RELATED APPLICATION

This application is a continuation-in-part of co-pending application Ser. No. 08/080,017, filed Jun. 18, 1994.

BACKGROUND OF THE INVENTION

Renal calculous disease is a common disorder in this country which has been suggested to be on the rise. In 1950, only 0.95 per one thousand Americans were estimated as having the disease. By 1984, this number had risen to 1.64 per one thousand Americans. Boyce, W. H. [1979] "Epidemiology of Lithiasis in the United States," XVIIIth C. M. Congress of the International Society of Urology, Paris, Kongressbericht, Tome 1, pp. 79–86. A 1978 report by Sierakowski et al. estimated that about 12% of the U.S. populace will suffer from stone disease at least once in their lifetime (Sierakowski, R., B. Finlayson, R. R. Landes, C. D. Finlayson, N. Sierakowski [1978] *Invest. Urol.* 16:438–441). That estimate would be expected to have increased substantially in accordance with the increased incidence of kidney stone disease.

The most prevalent type of renal stone disease is of a calcareous and idiopathic nature, occurring mostly in white males. Therefore, it is known that incidence of kidney stone disease is associated with gender and race differences. Geographic and dietary factors can also affect incidence.

Unlike normal biomineralization processes (e.g., bone and tooth formation), calcium oxalate urolithiasis is a pathological process. Although this process has been extensively studied, adequate therapy for the disease can be a highly complex and uncertain subject to the average medical practitioner. See Thomas, Jr., W. C., [1976] *Renal Calculi: A Guide to Management*, Charles C. Thomas, Publisher, Springfield, Ill., 177 pp. In addition, kidney stone disease can be an extremely painful experience for the patient. Passage of stones can cause renal colic, destruction of kidney tissue from mechanical irritation by the stone, as well as back pressure from obstruction of urinary flow. An increased risk of infection also accompanies the presence of any foreign body.

Crystallization within the urinary tract occurs opportunistically and quite freely. Formation of smaller crystallites is a normal renal function for eliminating calcareous stone salts. Abnormal conditions presumably result from uncontrolled crystal agglomeration and/or cellular attachment/retention of crystals. Stone disease arises when crystallite attachment is not blocked within the urinary tract. Consequently, further biomineralization and accretion of other cell debris and solutes create flow-obstructing kidney stones. Although certain factors, e.g., uncontrolled biosynthesis of oxalate (hyperoxaluria), elevated phosphate levels (phosphaturia), and excessive dietary intake of oxalate-rich foods can exacerbate stone formation, it remains an idiopathic disease.

The prevalence of kidney stone disease arising from pathological calcium oxalate biomineralization contributes substantially to the cost of health care in the United States. For example, costs for hospitalization and surgery or extensive outpatient extracorporeal shock-wave lithotripsy treatment of approximately 500,000 U.S. residents annually has been estimated at $3 billion. These figures exclude lost occupational time during treatment or recuperation. Davis et al. (Davis, G. K., N. B. Cummings, B. Finlayson, J. L. Meyer, M. J. V. Smith [1974] "Urolithiasis," in *Geochemistry and the Environment*, Natl. Acad. Sci., Washington, pp. 133–138) put the number of lost working days at nearly 15,000,000 annually in this country alone, which translates to around 56,000 person-years of productivity lost each year. An even more telling expression of the economic impact is that a work force of 56,000 corresponds to the productivity of an entire city of about 130,000 to 150,000. Thus, it is clear that a simple, accurate, and reproducible method for detecting or treating such conditions, even in advance of stone formation, is a valuable contribution to the management of kidney stone disease.

Previously, methods for detecting kidney stone formation or treating kidney stone disease have been described, but are quite different from the subject invention. For example, U.S. Pat. No. 5,137,722 describes an extract and pharmaceutical composition for treatment of calcium oxalate stone disease. The extract is purified from the plant *Edobotrya japonica*. The extract does not consist of any citrate-containing compounds.

U.S. Pat. No. 4,399,003 describes a method and kit for diagnosing a patient's proneness to develop calcium oxalate-type kidney stones. The method comprises measuring the rate of decrease of calcium ion concentration in the patient's urine sample as compared to a reference standard of normal urine. This method differs substantially from the diagnostic method described hereinbelow, which does not directly measure calcium ion concentration in the patients' urine.

U.S. Pat. No. 4,888,182 also describes methods and compositions for the treatment and prophylaxis of calcium renal stones. By contrast, the subject invention comprises a novel compound and methods of use which are clearly distinguishable from the citrate salt and methods of using that ionic salt as described in the '182 patent.

Except for a small fraction of stone-formers (e.g., individuals with primary hyperoxaluria, those with renal tubular acidosis, and others having chronic hypercalcemic disorders), there has been no clearly defined single criterion, or uniform set of criteria, that can be characterized for the much larger group of idiopathic kidney stone-formers, which are addressed by the subject invention.

A few other potential diagnostic tools for discerning urolithiasis have been described in the scientific or medical literature. Illustrative are the work of Zhmurov (Zhmurov, V. A. [1991] *Urol. Nefrol-Moscow* May–June (3):12–15), who found altered phospholipid composition in the urine of stone-formers, and Azoury et al. ([1990] *Urolog. Res.* 18:7–11) who described the use of nuclear magnetic resonance proton-relaxation-rates (PRR) to distinguish healthy and stone-former urine samples. The method of Zhmurov et al. has the obvious disadvantage of analyzing changes in complex patterns of phospholipid composition. With regard to the Azoury et al. method, the high cost of nuclear magnetic resonance instrumentation is a major contributing factor to its general unavailability in clinical laboratories.

The techniques described either by Zhmurov et al. or Azoury et al. have not been instituted as a commercial diagnostic measure. More fundamentally, the changes reported by Zhmurov et al. and Azoury et al. may relate to secondary pathophysiologic responses to the presence of kidney stones or to the absence of dicitrate cyclic diester (see discussion below), and they may not be generally applicable prior to the occurrence of stone disease.

The type of calculus evidenced in any particular patient is due primarily to a urinary deficiency of inhibitors normally present to help suppress crystal formation. Several compounds have been proposed as contributing factors in the inhibition of crystal formation. For example, Schreier et al. reported that about one-half of the inhibitory activity for calcium oxalate crystal growth in urine was due to compounds smaller than 5000 daltons, and that a portion of the activity had been shown to be due to pyrophosphate and titrate. Large molecular weight inhibitors in three families, e.g., glycosaminoglycans (GAGs), ribonucleic acids (RNAs), and glycoproteins, accounted for approximately 40% of total inhibition. The remainder of inhibitory activity was due to compounds which were chemically undefined. Thus, a variety of compounds have been suggested as potential inhibitors of kidney stones (Schreier, E. E., K. E. Lee, J. L. Rubin, P. G. Werness, L. H. Smith [1979] "Macromolecular Inhibitors of Calcium Oxalate Crystal Growth and Aggregation in Urine," In *Oxalate in Human Biochemistry and Clinical Pathology*(G. A. Rose et al., eds.), London, The Welcome Foundation, pp. 22–610).

It has been known for decades that urine can prevent cement from hardening properly. One of the current inventors described isolation, using column chromatography, of a fraction from urine which appeared to inhibit setting of cement. A citride compound was synthesized which reduced the ability of cement to harden, but it was not determined what the exact structure of the compound was. The compound was determined to be distinct from the water soluble di-, tri-, or tetramethyl citrate compounds isolated from pineapple in the course of preparing vitamin C, as described nearly sixty years ago. See Bose, P. K., S. N. Bhattacharyya (1936) *Science and Culture* 2:162. Moreover, it was undetermined what the role of the compound was in the inhibition of hardening of cement and whether there was any relation to kidney stone formation (Thomas, Jr., W. C. [1988] *Md. Med. J.* 37:861–862). Nor was it known whether this compound corresponded to a natural inhibitor or whether the compound was a single chemical species. Furthermore, there was no evidence then available to indicate that calcareous stone disease could be reliably linked to the absence of any single metabolite. The speculative nature of these studies proposing a role for inhibitors of calculus formation is evidenced by subsequent studies which continued to suggest that proteins, especially glycoproteins, played an important role in the inhibition of calcium oxalate crystal formation (Coe, F. L., Y. Nakagawa, J. H. Parks [1991] *Am. J. Kidney Disease* 17:407–413). However, epidemiological studies of certain substances, e.g., titrate, phosphate, pyrophosphate, glycosaminoglycans, nephrocalcin, Tamm-Horsfall proteins, and uropontin, showed that none of these substances can be used as an unambiguous, single-determinant marker for calcareous stone disease.

Accordingly, the development of prospective diagnostic techniques to identify those patients who are predisposed to developing kidney stones is needed to provide a means for mitigating these costs through the exercise of preventative practices by those predisposed patients. Therefore, the discovery of a singular, unambiguous marker as described hereinbelow is a substantial contribution to the art.

BRIEF SUMMARY OF THE INVENTION

The subject invention pertains to a method for distinguishing normal and kidney stone-forming patients based on the presence or absence of a novel compound, dicitrate cyclic diester or an analog, derivative, metabolic precursor, metabolite, or salt thereof. The presence of this compound in healthy patients and its absence in stone-forming patients offers definite advantages in its use as a diagnostic measure. By analyzing the dicitrate cyclic diester content in as little as 2–3 ml of urine, a predisposition to stone formation can be diagnosed before the occurrence of a stone episode. Kits which can be used, for example, for diagnostic purposes, can comprise the substantially pure novel compound or its analogs, derivatives, metabolic precursors, metabolites, or salts, or other component used to detect the novel compound.

The subject compound can also be synthesized by a novel method which employs the reaction of citrate with a dehydrating agent, e.g., dicyclohexyl carbodiimide.

Further, the subject compound, or a derivative, metabolite, or salt of the compound, and compositions comprising the subject compounds can be employed in a novel method for inhibition of calcification applicable to the prevention or treatment of calcification-related diseases, e.g., kidney stone disease.

It is another object of the invention to utilize the metal ion complexing properties of the subject compounds to reduce the concentration of free metal ions where they are undesired. Thus, it is considered that the subject invention includes the use of the subject compounds as complexing agents to bind with, and reduce the amount of, free metal ions associated with certain diseases or with metal toxicity or contamination. Complexing agents are also useful as inhibitors of food discoloration caused by the presence of metal ions. Therefore, the compounds can also be used to complex metal ions in foods and prevent the discoloration of foods.

DETAILED DISCLOSURE OF THE INVENTION

Figure 1:
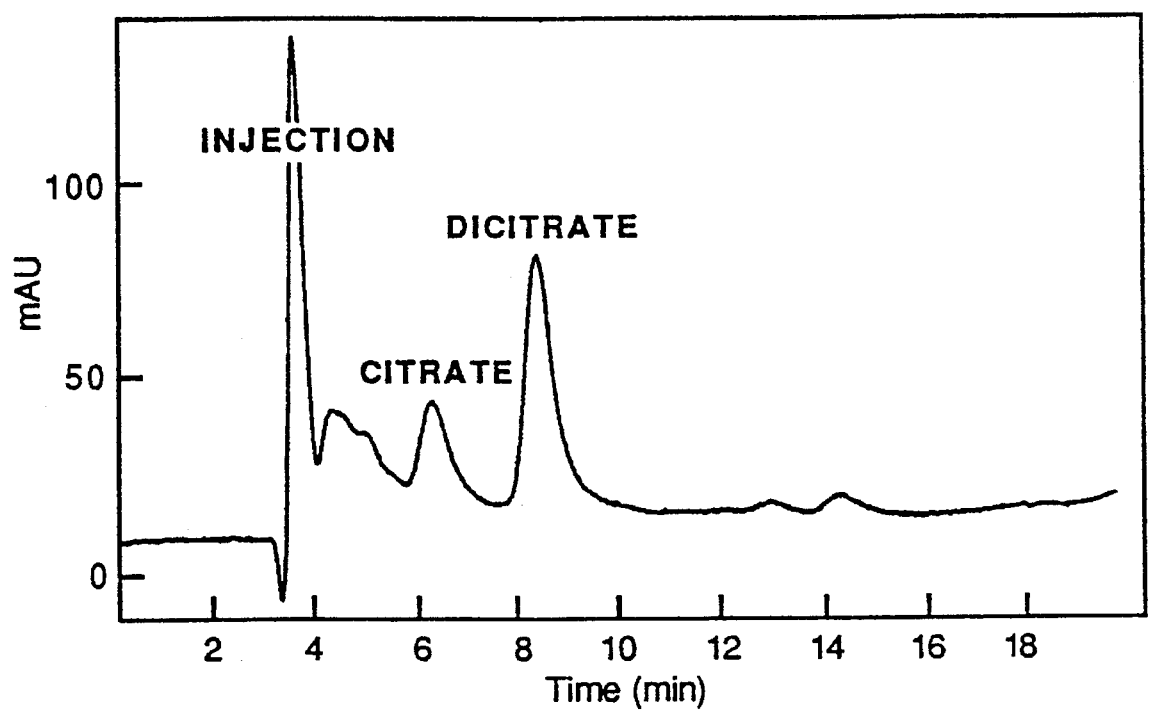
FIG. 1 is an HPLC profile of synthetic dicitrate cyclic diester (8.3 minutes) and citrate (6 minutes). The peak at approximately 4 minutes is the injection, or solvent, peak.

We discovered a novel urinary metabolite in the urine of humans who show no symptoms of, or no predisposition to, renal calculous disease. Our findings demonstrated that the major urinary inhibitor of hydroxyapatite crystal formation is a citrate-rich acidic compound having a molecular mass of less than 2,000 Daltons and having the general structure:

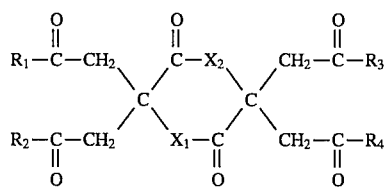

wherein $R_1$, $R_2$, $R_3$, and $R_4$ can be the same or different and can be OH, O—$(CH_2)_nCH_3$, wherein n=1–50, O-aryl, NH, N-alkyl, or N-aryl; and $X_1$ and $X_2$ can be the same or different and can be O or NH. In a preferred embodiment, the compound is dicitrate cyclic diester, wherein $R_1=R_2=R_3=R_4=$OH and $X_1=X_2=$O. Dicitrate cyclic diester is also referred to herein as "dicitrate" and means dicitrate cyclic diester and any analogous form, derivative, metabolite, or salt thereof. These analogs, derivatives, metabolic precursors, metabolites, or salts of the subject compound would be readily recognized by a person of ordinary skill in the art. For example, a metabolic precursor would be recognized as an uncyclized mono- or diester of the subject compound, or a proform of the subject compound which can include the compound or its precursor associated with, or bound to, a peptide or coenzyme or other molecule which is cleaved from the compound when biologically transformed or metabolized in the body. The compound formed by esterification of citrate with itself can also include uncyclized dimer, as well as trimers or other polymers. The novel compound can be isolated using a novel chromatographic procedure, as described herein, or can be synthesized by chemical or biotechnological procedures.

In chemical synthesis of the novel dicitrate cyclic diester compound, citrate and a dehydrating agent, e.g., dicyclohexyl carbodiimide, carbonyl diimidazole, other diimide-based agents and the like, can be used as starting materials. To synthesize the diester, the diimide compound and citrate are typically provided at a ratio of 1:2. When the citrate is provided at less than twice the molar amount of the diimide, e.g., at a ratio of 1:1 or less, a dicitrate monoester intermediate can be formed. The monoester can be formed as an intermediate by metabolic processes in the body as well.

The novel compound can be synthesized by a dehydration reaction in the presence of tetrahydrofuran (THF). Preferably, the citric acid and THF are provided in their anhydrous forms. Other compounds which can be used in this reaction would be recognized by those of ordinary skill in the art. For example, other carboxylic acids, e.g., tartaric acid, isocitric acid, or 3-amino citric acid, can be used as starting material with citrate to produce structural analogs of dicitrate. Other solvents, e.g., pyridine, and various aqueous buffers, can also be used in place of, or in addition to, THF.

A novel method for detecting the presence of the subject compound in a biological sample is also described. Preferably, the biological sample is subjected to a separation procedure as a clean-up step, essentially fractioning the dicitrate cyclic diester from undesired compounds in the biological sample. The biological sample is typically urine or blood but can be other body fluids, including saliva or other digestive fluids, lymphatic fluid, or other intra- or extracellular fluid or tissue where dicitrate is present at detectable levels. The separation technique comprises the utilization of column chromatography which can further comprise a first step of separating the target compound from the sample, e.g., urine, on a gel permeation column. Typically, a chromatography column using Sephadex G-25 as the stationary phase can be used to adsorb the target compound in this initial step. The compound can be eluted from the stationary phase with a salt solution, preferably a carbonate salt solution, for example, ammonium carbonate.

Citrate-containing fractions can then be further separated by ion-exchange column chromatography. These titrate-containing fractions can be determined colorimetrically. Due to the charge associated with citrate, anion exchange resins are preferred as the stationary phase for the ion-exchange chromatography step. The dicitrate fraction eluted from the ion-exchange column is then passed through a second gel permeation column, eluted, and lyophilized. The lyophilized residue can then be redissolved in water for subsequent detection, which is preferably by high performance liquid chromatography (HPLC) analysis. A typical HPLC elution profile is presented in FIG. 1, wherein the three peaks above zero absorbance are the solvent, or injection, peak (elution time 2–4 minutes), the citrate peak (maximal at 6 minutes), and the dicitrate cyclic diester peak (present at 8.3–8.6 minutes).

Figure 2A:
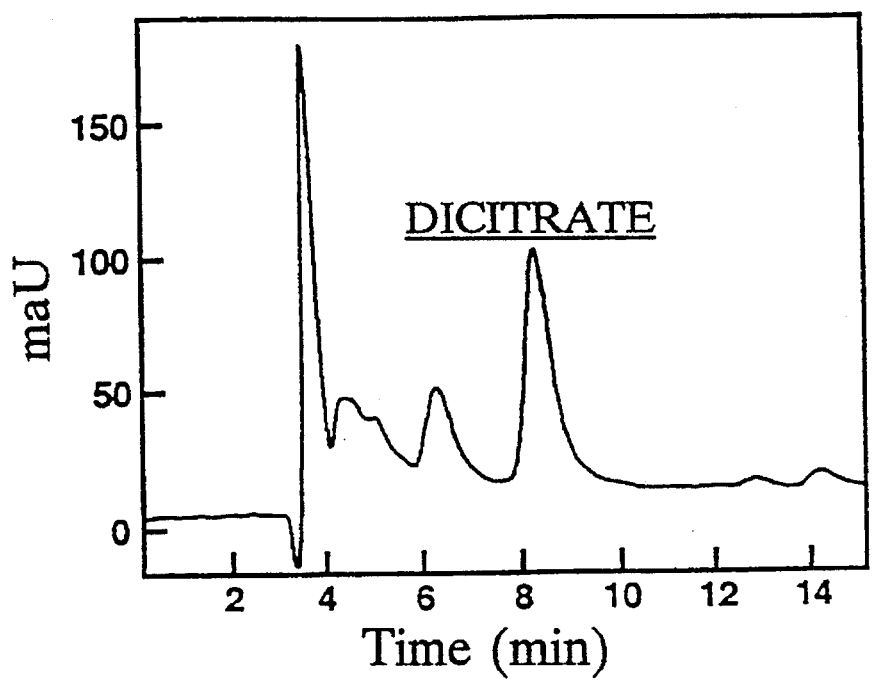
FIG. 2*a* shows an HPLC elution profile of a urine sample obtained from a healthy subject.
Figure 2B:
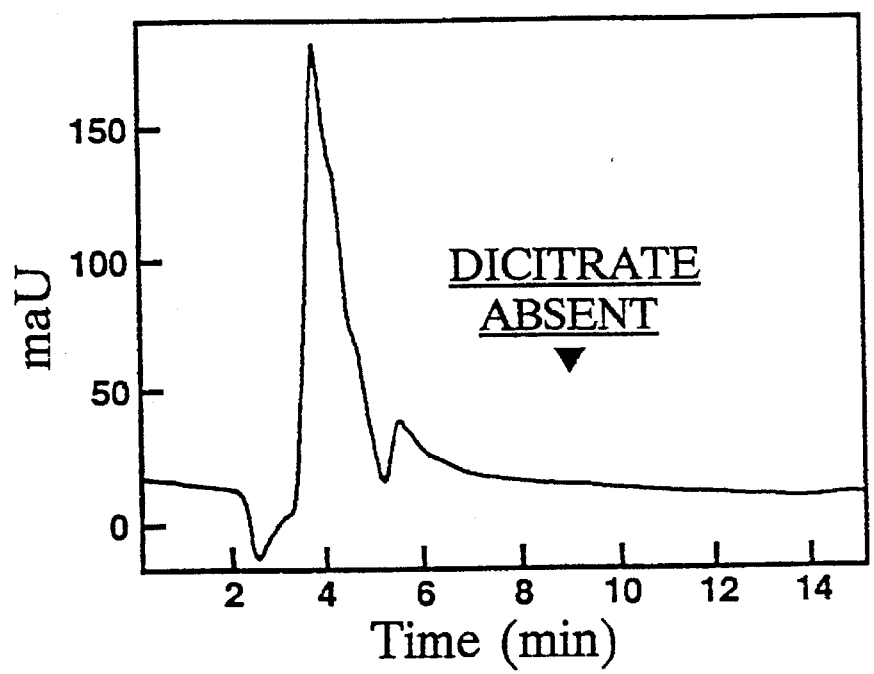
FIG. 2*b* shows an HPLC elution profile of a urine sample obtained from a calculous patient.

By applying these separation and detection methods to urine samples from healthy and calculous patients, we have observed that the dicitrate cyclic diester peak is absent in samples from patients with renal calculi (see FIGS. 2a–2b). Determinations of the presence of dicitrate cyclic diester in urine were conducted in a completely blinded experimental procedure and, in all cases, healthy patients showed clear evidence of a dicitrate cyclic diester peak, and kidney stone patients showed no dicitrate cyclic diester peak above the baseline of the elution profile. Furthermore, in one case where additional citrate was administered orally to a kidney stone patient, we observed a prominent citrate peak, but no dicitrate cyclic diester was evident even though the dietary intake of citrate was relatively high.

Thus, the presence or absence of dicitrate cyclic diester is an advantageous and valuable diagnostic determinant for identifying individuals likely to develop kidney stones. Other disease conditions including, but not limited to, formation of atheromas in arteriosclerosis, hypercoagulation of blood which has been indicated in microvasuclar stroke, calcium deposition on bone, e.g., bone spur formation, dental calculus formation, as well as the genesis of gallstones, can also involve pathologic calcification processes, and are considered to be pathologic calcification conditions for purposes of the subject invention. Dicitrate cyclic diester can be used as a clinical marker and for treatment of these conditions. Preferably, the presence of dicitrate cyclic diester can be detected by the novel HPLC method described herein. However, the detection of dicitrate cyclic diester in human fluids can include the utilization of other methods including, but not limited to, adsorption/ion-exchange chromatography, colorimetry, electrophoresis, ultraviolet/visible/infrared/Raman spectroscopy, gas chromatography, mass spectrometry, and immunochemical and biochemical techniques. These detection techniques can involve the production of derivatives of dicitrate prior to analysis.

Kits comprising a separately packaged dicitrate, precursor, metabolite, or reactant can be advantageously used in the diagnosis and treatment of pathologic calcification conditions. For example, a simple colorimetric test for diagnosing the presence of dicitrate can be packaged as a kit which comprises neutral 4M hydroxylamine and ferric chloride solution. Following the mixture of the biological sample to be tested with the hydroxylamine, ferric chloride solution can be added to yield a colored reaction product detectable at approximately 540 nm. The detection of dicitrate cyclic diester can result from direct or indirect detection of the compound. Therefore, it should be understood that other forms of the compound can be what is actually detected. For example, detection of a metabolic precursor or intermediate of dicitrate cyclic diester or a metabolic product therefrom can be the equivalent of detecting the compound itself. Moreover, the detection of an enzyme which can catalyze the biosynthesis of dicitrate or, alternatively, detecting the absence of an enzyme which can metabolize dicitrate to its breakdown product(s) can also effectively be used to detect the presence or absence of dicitrate.

It is also understood that antibodies can be made to the novel dicitrate compound, or its analog, derivative, or salt, or antibodies to a metabolic enzyme involved in the biosynthesis or biotransformation of dicitrate. These procedures for antibody production are standard in the art and could be readily conducted by persons of ordinary skill in the art. For example, antibodies can be raised to the dicitrate compound itself or using the compound as a hapten conjugated to an acceptable carrier, wherein the carrier is an immunogen. These antibodies can be useful for purification procedures, e.g., affinity chromatography, for immunoassay or diagnostic kits, for therapeutics, and other methods and procedures where antibodies typically can be employed. An assay employing specific antibodies to detect dicitrate can involve recognition, i.e., binding, of the antibody to the compound or the compound-specific moiety of a hapten-carrier conjugate. The antibody can be labelled by any available means, e.g., radioactive or enzymatic markers, or can be further recognized by a second antibody having a label.

Dicitrate cyclic diester is a potent inhibitor of hydroxyapatite and calcium-oxalate crystal formation. Our studies indicate that at least one step in stone formation (i.e., nucleation, growth, aggregation, or crystal retention on renal tubular surfaces) is blocked by this novel renal calcification inhibitor (see Example 5). Novel treatments for kidney stone disease and other pathologic calcification processes can also be accomplished by administration of dicitrate cyclic diester, analogs, metabolites, derivatives, or salts thereof, or compositions comprising the compound or one of its analogs, derivatives, metabolites, or salts. Thus, dicitrate can be useful for prophylactic or therapeutic treatment of a calcification process, including idiopathic kidney stone disease or other pathologic calcification.

The treatment of patients with pathologic calcification diseases, or symptoms thereof, can be carried out by administering to these patients an effective amount of the compound, itself, or its metabolic precursor, analog, derivative, metabolite, or salt, or a composition comprising the novel compound, its precursor, analog, derivative, metabolite, or salt. The compound used in these compositions can be isolated and purified from biological sources, can be chemically synthesized, or can be produced using biotechnology procedures.

Preferably, the novel compound is therapeutically administered orally or parenterally or can be provided as a dietary supplement. However, as exemplified below, other routes of administration of the novel compound can also be employed.

Because chelation of a metal ion, e.g., Fe(II), Fe(III), Al(III), and the like, results in high affinity complexes, dicitrate cyclic diester, which exhibits chelating activity can be useful as a metal ion complexing agent in controlling, i.e., lowering, the concentration of these and other free metal ions which are associated with pathological conditions. Pathological conditions associated with abnormal free metal ion concentrations include, for example, Wilson's disease, Alzheimer's disease, and reperfusion injury often seen in patients with heart attack or spiral injuries.

The methodology for complexing metal ions can also be used in treating heavy metal poisoning in an animal or human such as that seen with cadmium, lead, strontium, arsenic, and the like. It would also be understood that the subject compounds can be used as a complexing agent to bind with, and thus reduce the concentration of, free metal ions, including heavy metal contaminants in the environment. For example, the dicitrate can be used as a treatment or in a filter to remove heavy metals from an environmental substance, such as water, soil, or air where heavy metals may be present, by contacting the compounds with the biological or environmental substance.

It is also known that certain free metal ions can discolor food. Thus, dicitrate can also be used as a complexing agent to reduce the free metal ion concentration in foods, thus inhibiting the process resulting in food discoloration. The methodology employed in these additional uses for dicitrate as a free metal ion complexing agent would be readily understood by those of ordinary skill in the art.

Following are examples which illustrate procedures, including the best mode, for practicing the invention. These examples should not be construed as limiting. All percentages are by weight and all solvent mixture proportions are by volume unless otherwise noted.

EXAMPLE 1

Isolation of Dicitrate Cyclic Diester from Urine or Serum Samples

An aliquot (20 ml) of urine collected over the 24-hour period (each specimen combined and refrigerated during the collection) was passed through a Sephadex G25 gel permeation column. The sample was eluted with 5 mM ammonium carbonate, and the citrate-containing fractions, were identified colorimetrically, then pooled, and lyophilized. The sample was redissolved in water and passed through a Dowex AG1X8 anion-exchange chromatography column. Samples were eluted with increasing concentrations of ammonium carbonate (linear gradient from 100 mM to 700 mM), and the citrate-containing fractions were again pooled and lyophilized. The solid is redissolved in water and passed through a second Sephadex G-25 column, and citrate-containing fractions were pooled and lyophilized. An identical procedure is used to obtain the major calcification inhibitor fraction from a 20 ml sample of human serum.

EXAMPLE 2

High Performance Liquid Chromatography Analysis

The citrate-containing fractions obtained by the column chromatographic methods described above were redissolved in 0.5–1.0 ml water and applied to a C-18 reverse-phase chromatography column using a Hewlett-Packard 1090a high volume liquid chromatograph. Samples were eluted isoelectrically with one percent (volume/volume) trifluoroacetic acid in acetonitrile, and detected by UV absorbance at 214 nm.

EXAMPLE 3

Detection of Dicitrate Cyclic Diester in Biological Samples

Following separation procedures as described herein, HPLC analysis of patients' urine samples consistently showed the complete absence of the dicitrate cyclic diester peak in those patients with renal calculi. Illustrative are the results of one set of determinations with a healthy subject and a calculous patient shown in FIGS. 2a and 2b. We conducted additional blind studies, of which the experimental results were subsequently decoded by one or more of the inventors. In all cases, healthy patients showed clear evidence of a dicitrate cyclic diester peak, whereas kidney stone patients had no discernable dicitrate cyclic diester peak above the baseline of the elution profile. Even stone patients having relatively high titrate supplements added to their diet did not subsequently show a dicitrate cyclic diester peak on HPLC analysis. Therefore, the absence of dicitrate cyclic diester in a stone patient does not result simply from reduced availability of a titrate precursor. Moreover, two patients with uric acid stones (a condition which is not at all related to calcareous renal calculi) were observed to have dicitrate cyclic diester in their urine. We also found that patients who form calcium oxalate stones as a result of hyperparathyroidism have dicitrate cyclic diester in their urine. Thus, dicitrate cyclic diester determinations can be used as a marker of idiopathic calcium oxalate urolithiasis, and allow the idiopathic stone formation to be distinguished from other hormone-related kidney stone disease. The results of these studies are shown in Table 1, below.

TABLE 1

A summary of clinical dicitrate determinations by HPLC

| Subject | Age | Sex | Diagnosis | Detectable Urinary DCD |
|---------|-----|-----|-----------|------------------------|
| D. C. | 32 | M | Idiopathic Stones | No |
| N. C. | 32 | M | Idiopathic Stones | No |
| L. Q. | 37 | F | Idiopathic Stones | No |
| R. N. | 33 | M | Idiopathic Stones | No |
| J. A. | 37 | M | Incomplete RTA | No |
| B. P. | 32 | M | Normal | Yes |
| L. H. | 31 | M | Normal | Yes |
| W. T. | 63 | M | Normal | Yes |
| L. S. | 50 | F | Normal | Yes |
| B. B. | 39 | M | Normal | Yes |
| B. G. | 39 | F | Uric Acid Stones | Yes |
| B. S. | 57 | M | Uric Acid Stones | Yes |
| V. C. | 59 | M | Hyperparathyroidism | Yes |
| R. K. | 50 | F | Hyperparathyroidism | Yes |

DCD = dicitrate cyclic diester

All of our experimental results consistently segregate healthy and stone-forming subjects, and they demonstrate the utility of our method in the prospective detection of kidney stone patients.

EXAMPLE 4

Application of Dicitrate to Other Pathological Calcification Processes

The dicitrate compound, and methods of use involving detection of the compound or its prophylactic or therapeutic administration, have been described herein as primarily relating to renal calculus. Other important pathologic calcification processes can also benefit from the detection or administration of dicitrate. These include, but are not limited to, the following conditions:

A. Coagulation

Blood coagulation is exquisitely sensitive to the concentration of calcium ion which is an essential activator of many calcium-activated enzymes responsible for both intrinsic and extrinsic clotting pathways. A steady normo-calcemic state in humans is effectively maintained by two hormonal factors: (a) calcitonin, which inhibits bone calcium mobilization, thereby suppressing a rise in circulating calcium ion concentration; and (b) parathyroid hormone, which mobilizes bone-dissolving osteoclasts to release calcium into circulation and which enhances renal tubular reabsorption of calcium ion. Because ionic calcium (i.e., uncomplexed $Ca^{2+}$) is the most likely feedback signal, circulating calcium ion-binding metabolites can act as hypocalcemic agents and suppress coagulation. The hitherto unrecognized absence of dicitrate cyclic diester in calcareous stone patients promotes hypercoagulation. Thus, elevation of dicitrate concentration in the blood of stone patients comparable to normal circulating concentrations of dicitrate in the blood of healthy subjects can be useful in suppressing coagulation. Inhibition of hypercoagulation is a recognized treatment or preventive measure against microvascular stroke. Dicitrate can therefore be an especially important substitute for heparin sulfate, which is typically used clinically to inhibit coagulation during angioplasty and other procedures requiring suppression of patient blood clotting.

B. Arteriosclerosis

Hardening of the arteries (or arteriosclerosis) is a circulation-obstructing disease involving calcification. One example is intimal arteriosclerosis in which fatty deposits form in the blood vessel lining followed by pathologic calcification of the arterial middle layer (or media). Another form of arteriosclerosis occurs as a result of scar tissue formation on the vessel lining as well as calcification. Ultimately, loss of vessel elasticity and concomitant increase in blood pressure arises as the level of calcification hardens the blood vessel lining. Because dicitrate cyclic diester suppresses pathological calcification, our discovery that dicitrate is present in healthy patient blood indicates that this agent can be used to suppress arteriosclerosis in healthy patients. Therefore, elevation of circulating dicitrate to concentrations can inhibit the course and severity of arterial vessel hardening.

C. Dentifrices/Calculus-Inhibiting Mouthwashes

Because oral pathological calcification is a causative factor in periodontal disease, various toothpastes and mouthwashes are formulated with pyrophosphate salts which bind free calcium and thereby reduce the thermodynamic driving force for calculus formation on teeth. Our discovery of dicitrate cyclic diester as a hitherto unrecognized naturally occurring inhibitor of pathological calcification indicates that dentifrice and mouthwash formations can be a beneficial treatment in the prevention of calculus accumulation. Furthermore, because dicitrate acts in two different ways (i.e., binding to free calcium ion and binding to calcified surfaces), this metabolite can offer advantageous properties as compared with exclusively calcium ion-binding agents such as pyrophosphate.

EXAMPLE 5

Non-Therapeutic Application of Dicitrate

In view of the advantageous calcium-binding properties of dicitrate, it would be recognized by those of ordinary skill in arts related to, as well as unrelated to, the medical arts that dicitrate, or compositions comprising dicitrate, can have utility in non-therapeutic applications. For example, in the arts of laboratory science or blood product analysis, collection, or utilization, the dicitrate can be used as an anticoagulant in blood collection tubes, in intravenous or intra-arterial catheters, or other like applications where coagulation of blood can be detrimental to the work being conducted.

Alternatively, inhibition of calcification processes can be useful in non-medical fields. For example, calcification on the interior walls of water pipes or plumbing facilities can create problems, especially in geographic areas where high calcium is present in the water supply. Dicitrate has the advantageous properties of binding free calcium ions and thereby can prevent the buildup of calcium on the inner walls of water pipes and the like. A composition comprising dicitrate can be applied to water lines or can be coated onto or incorporated into the water pipes or plumbing fixtures to resist the initiation of the calcification process. Thus, it is contemplated by the inventors that the dicitrate and compositions comprising dicitrate can be used in ways to prevent these non-pathologic calcification processes. Other calcification processes which involve free calcium ion or calcium salt deposition can also be inhibited by the subject dicitrate.

EXAMPLE 6

Synthesis of Dicitrate Cyclic Diester

Anhydrous citric acid (5 mmoles, 960 mg) and dicyclohexyl carbodiimide (10 mmoles, 2.06 g) were stirred in 30 ml anhydrous tetrahydrofuran for one hour. Dicyclohexylurea crystals formed during the ensuing dehydration reaction were removed by filtration, and the filtrate was dried in vacuo, yielding the dicitrate cyclic diester-containing solid residue.

The synthetic conversion of citric acid and dicyclohexyl carbodiimide into dicitrate cyclic diester was confirmed both by HPLC elution characteristics and as mass spectrometry. As shown in FIG. 1, dicitrate and citrate have well-defined chromatographic properties, and the additional ionic charge of dicitrate results in its correspondingly greater retention time for isocratic elution. In addition, the mass of the molecular ion was found to be 348.1 using a Finnigan time-of-flight quadrapole mass spectrometer, equipped for laser desorption of ionic samples. This value corresponds to mass predicted on the basis of the dicitrate cyclic diester structure.

EXAMPLE 7

Dicitrate Inhibition of Calcification

Dicitrate demonstrates potent inhibitory properties in two different calcification assays. In the first, we used a tendon mineralization assay with supersaturated solutions of calcium and phosphate (Thomas, W. C., Jr., A. Tomita [1967] *Am. J. Pathol.* 51:621–628). Bovine Achilles tendon served as the biological matrix material for mineralization in buffered solutions containing calcium ion (3–7 mg/liter) and phosphate (2–5 mg/liter) in the absence or presence of 3–5 mM citrate or dicitrate. In this assay, dicitrate was 12–14 times more effective than an equivalent concentration of citrate in inhibiting the formation of crystals in the collagen fibrils of the tendon.

In the second calcification protocol (Antinozzi, P. A., C. M. Brown, D. L. Purich [1992] *J. Crystal Growth* 125:215–222), calcium chloride dihydrate and potassium oxalate are added to a buffered solution consisting of 0.1M sodium chloride and 0.01 M N,N '-hydroxyethylpeperazineethanesulfonate (pH 6.5) at a relative supersaturation (i.e., the calcium oxalate ion-activity product divided by the equilibrium solubility product) of 18. The presence of 5 mM dicitrate inhibited the rate of calcium oxalate crystallization by a factor of 5–8 relative to an equivalent concentration of citric acid.

EXAMPLE 8

Formulations

The compounds of the invention are useful for various non-therapeutic and therapeutic purposes. It is apparent that the compounds of the invention are effective for inhibiting kidney stone formation and for other calcification process-related diseases. Specifically exemplified herein is the control of idiopathic renal calculous disease.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the calcification disease and the age, health, and weight of the patient as well as the kind of concurrent treatment, if any, frequency of treatment, therapeutic ratio, and like considerations.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

The compositions of the invention are advantageously used in a variety of forms, e.g., tablets, ointments, capsules, pills, powders, aerosols, granules, and oral solutions or suspensions and the like containing the indicated suitable quantities of the active ingredient. Such compositions are referred to herein and in the accompanying claims generically as "pharmaceutical compositions." Typically, they can be in unit dosage form, namely, in physically discrete units suitable as unitary dosages for human or animal subjects, each unit containing a predetermined quantity of active ingredient calculated to produce the desired therapeutic or prophylactic effect in association with one or more pharmaceutically acceptable other ingredients, e.g., diluent or carrier.

Where the pharmaceutical compositions are aerosols, the active ingredients can be packaged in pressurized aerosol containers with a propellant, e.g., carbon dioxide, nitrogen, propane, etc. with the usual adjuvants such as cosolvents, wetting agents, etc.

Where the pharmaceutical compositions are ointments, the active ingredient can be mixed with a diluent vehicle such as cocoa butter, viscous polyethylene glycols, hydrogenated oils, and such mixtures can be emulsified if desired.

In accordance with the invention, pharmaceutical compositions comprise, as an active ingredient, an effective amount of one or more non-toxic, pharmaceutically acceptable ingredient(s) or carriers.

Examples of such carriers for use in the invention include ethanol, dimethyl sulfoxide, glycerol, silica, alumina, starch, and equivalent carrier and diluents. While effective amounts may vary, as conditions in which such compositions are used vary, a minimal dosage required for activity is about 50 micrograms. To provide for the administration of such dosages for the desired therapeutic treatment, new pharmaceutical compositions of the invention will advantageously comprise between about 0.01% and about 50%, and especially, about 0.1% and about 30%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg; dermally 0.01 to about 500 mg/kg and preferably about 1 to 100 mg/kg; intranasal instillation, 0.01 to about 20 mg/kg; and aerosol, 0.01 to about 20 mg/kg of animal (body) weight.

The compounds of the subject invention can be parenterally, orally, or topically administered to subjects requiring treatment. The active compounds may be mixed with physiologically acceptable fluids such as saline or balanced salt solutions. Also, solid formulations such as tablets or capsules can be made using enteric coatings or other excipients which are known in the art.

The compounds of the subject invention may be applied, for example, orally, intravenously, intramuscularly, intraperitoneally, intranasally, intradermally, or subcutaneously. The compounds of the subject invention may also be combined with other substances to provide enhanced treatment.

It should be understood that the examples and embodiments described herein are for illustrative purposes only and that various modifications or changes in light thereof will be suggested to persons skilled in the art and are to be included within the spirit and purview of this application and the scope of the appended claims.

We claim:
1. A method for inhibiting calcification, said method comprising the application or administration of dicitrate cyclic diester, or salt thereof.
2. A method for treating a pathologic calcification condition, said treatment comprising the administration to a patient of an effective amount of dicitrate cyclic diester, or salt of said compound.
3. The method, according to claim 2, wherein said pathologic calcification condition is manifested as a condition selected from the group consisting of kidney stone disease, arteriosclerosis, blood coagulation or hypercoagulation, gall stones, bone calcium deposits, and dental calculus.
4. The treatment, according to claim 2, wherein said administration of said compound is a prophylactic treatment.
5. The treatment, according to claim 2, wherein said administration of said compound is a therapeutic treatment.
6. The method, according to claim 2, wherein said treatment comprises the oral administration of said compound to a patient.
7. The method, according to claim 6, wherein said oral administration is in the form of a dietary supplement.
8. A pharmaceutical composition comprising dicitrate cyclic diester or salt thereof, and a pharmaceutically acceptable carrier.

* * * * *

UNITED STATES PATENT AND TRADEMARK OFFICE
CERTIFICATE OF CORRECTION

PATENT NO. : 5,607,964

DATED : March 4, 1997

INVENTOR(S) : Hall *et al.*

It is certified that error appears in the above-indentified patent and that said Letters Patent is hereby corrected as shown below:

The text at Column 1, lines 10 & 11: should appear at Column 1, line 4.

Column 2, line 29: "*Edobotrya japonica.*" should read --*Eriobotrya japonica.*--

Column 3, line 18: "titrate." should read --citrate.--;

line 56: "titrate, phosphate," should read --citrate, phosphate,--.

Column 5, line 63&64: "titrate-containing" should read --citrate-containing--

Column 8, line 26: "fractions,were" should read --fractions were--

Column 9, line 1: "high titrate" should read --high citrate--;

line 5: "a titrate precursor." should read --a citrate precursor.--

Signed and Sealed this

Seventh Day of October, 1997

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,607,964
DATED : March 4, 1997
INVENTOR(S) : Thomas, Jr. et al.

It is certified that error appears in the above-identified patent and that said Letters Patent is hereby corrected as shown below:

The text at Column 1, lines 10 & 11: should appear at Column 1, line 4.

Column 2, line 29: "*Edobotrya japonica.*" should read --*Eriobotrya japonica.*--

Column 3, line 18: "titrate." should read --citrate.--;

line 56: "titrate, phosphate," should read --citrate, phosphate,--.

Column 5, line 63&64: "titrate-containing" should read --citrate-containing--

Column 8, line 26: "fractions,were" should read --fractions were--

Column 9, line 1: "high titrate" should read --high citrate--;

line 5: "a titrate precursor." should read --a citrate precursor.--

This certificate supersedes Certificate of Correction issued October 7, 1997.

Signed and Sealed this

Twenty-third Day of June, 1998

*Attest:*

BRUCE LEHMAN

*Attesting Officer*     *Commissioner of Patents and Trademarks*